Figure 1:
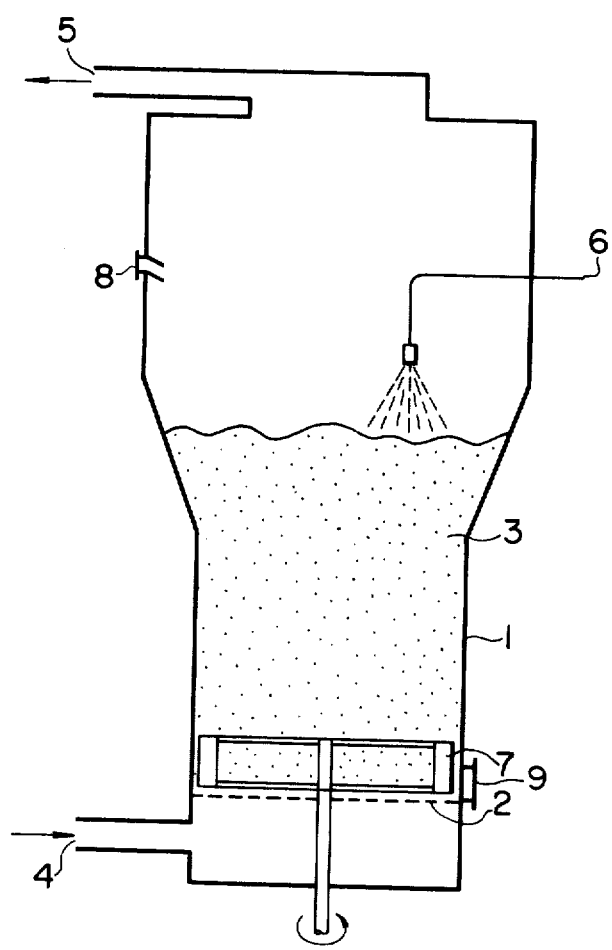

United States Patent [19]

Akao et al.

[11] 4,046,921
[45] Sept. 6, 1977

[54] PROCESS FOR CULTIVATING MICROORGANISMS BY MEANS OF FLUIDIZED BED

[75] Inventors: Takeshi Akao; Toshio Sakasai, both of Noda; Yoshikazu Matsuyama, Nagareyama; Yukio Kasuga, Takasago, all of Japan

[73] Assignee: Kikkoman Shoyu Co., Ltd., Noda, Japan

[21] Appl. No.: 655,130

[22] Filed: Feb. 4, 1976

[30] Foreign Application Priority Data

Feb. 5, 1975 Japan .................... 50-14290

[51] Int. Cl.$^2$ ............................ A23L 1/20
[52] U.S. Cl. ........................ 426/46; 426/52; 195/109; 195/142; 195/143; 195/144
[58] Field of Search ........... 195/139, 142, 143, 144, 195/109, 108; 426/46, 52

[56] References Cited

U.S. PATENT DOCUMENTS

| | | | |
|---|---|---|---|
| 3,123,475 | 3/1964 | Wendt et al. | 195/109 |
| 3,384,553 | 5/1968 | Coslansky et al. | 195/109 |
| 3,635,796 | 1/1972 | Imada et al. | 195/143 |
| 3,672,953 | 6/1972 | Coty et al. | 195/109 |
| 3,740,320 | 6/1973 | Arthur | 195/143 |

FOREIGN PATENT DOCUMENTS 27,488  5/1964  Japan .................... 195/109

OTHER PUBLICATIONS

H. H. Weetall, Food Products Development, vol. 7, No. 3, pp. 94-100; 1973.

*Primary Examiner* — Lionel M. Shapiro
*Assistant Examiner* — Robert J. Warden
*Attorney, Agent, or Firm* — Schuyler, Birch, Swindler, McKie & Beckett

[57] ABSTRACT

A process for cultivating microorganisms by means of fluidized bed characterized by cultivating a microorganism on a solid culture medium while mixing the solid culture medium in the fluidized bed with an upward gas stream and supplying an atomized liquid into the culture. According to this process, a cultivated product being high in enzymatic activity and quality is obtained with a high efficiency.

39 Claims, 1 Drawing Figure

PROCESS FOR CULTIVATING MICROORGANISMS BY MEANS OF FLUIDIZED BED

This invention relates to a process for cultivating a microorganism by means of fluidized bed. More particularly, it relates to a process for cultivating a microorganism for use in the fermentation industry, food industry, pharmaceutical industry, etc. by using a solid culture in a state of a fluidized bed.

The koji-making apparatus referred to in Japanese Patent Publication No. 27488/1964 is the only one cultivating apparatus of fluidized type ever disclosed. Since this apparatus is provided with no device for supplying effective water in the course of koji preparation, the water in the system is lost by evaporation in the course of koji-making. As a result, there occurs an extreme dryness of the koji itself and its effective water content cannot be maintained on the necessary significant level, unless an extremely large quantity of water is added to the koji at the start of koji-making process. Thus, the growth of microorganism cannot be controlled readily and the enzymatic activity of the product decreases greatly. If the water content of koji is increased at the beginning stage of koji-making, the koji becomes susceptible to the contamination with miscellaneous bacteria other than the cultivated microorganism so that the control of koji-making becomes quite complicated.

The present inventors conducted extensive studies with the aim of overcoming the above-mentioned drawbacks of the disclosed process. As a result, the present inventors have found that a cultivated product being high in enzymatic activity and quality can be obtained with a high efficiency by blowing a gas into the starting material of a solid culture from downside to bring the material into the state of a fluidized bed, supplying an atomized liquid into the resulting fluidized bed either continuously or intermittently, and thereby controlling the cultivation conditions. Based on the above-mentioned finding, this invention has been accomplished.

An object of the present invention is to provide a process for cultivating microorganisms by means of fluidized bed characterized by cultivating a microorganism on a solid culture medium while mixing the solid culture medium in the state of fluidized bed with an upward gas stream and supplying a liquid in an atomized state into the solid culture.

Other objects and advantages of the present invention will be apparent by the following descriptions.

The process of this invention is advantageous in that the characteristic property of a fluidized bed, namely the capability of powerful stirring and homogeneous mixing, can be exhibited to the greatest extent, and thereby that the cultivation conditions can be controlled as readily as if the culture used were liquid.

The starting material of the solid culture used in practising this invention includes at least one member selected from the group consisting of protein materials such as globular soy bean, defatted soy bean, wheat gluten, corn gluten, concentrated proteins, isolated proteins and the like or starch materials such as wheat, bran, barley, rice, starch and the like. These starting materials are subjected to ordinary denaturing and sterilizing treatments such as steaming, puffing, parching, roasting, etc. in advance. If necessary, said starting material may further be incorporated appropriately with an inorganic salt such as calcium chloride, magnesium sulfate, potassium sulfate and the like; vitamines; etc.

Although the starting material of the solid culture may have any size so far as it can be fluidized, it is preferred that it has a small average size of about 0.07 to 1.0 mm, particularly about 0.1 to 0.5 mm. In case a starting material of extremely small size is used, the water content of culture must be maintained at a low value. Otherwise, the culture will not be able to remain in the state of a uniform fluidized bed.

One may supply an atomized liquid into the solid culture by, for example, continuously or intermittently feeding a liquid which has been atomized with, for example, a high-pressure spraying nozzle or a pneumatic atomizing nozzle at the rate of about 10 to 250% (v/w) usually about 15 – 150% (v/w) and preferably about 20 – 130% (v/w), on the bases of the total quantity of the culture. The upper limit of the feeding rate may be higher than above if the object or the state of cultivation needs it. The liquid to be sprayed is either water itself or water incorporated with a nutrient such as minerals, vitamins, amino acids, culture itself and the like; or a pH regulator such as organic salts (e.g. sodium citrate, potassium citrate, sodium acetate, sodium lactate, sodium malate, sodium gluconate, sodium succinate or the like) and inorganic salts (e.g. sodium borate, sodium carbonate, sodium phosphate, sodium biphosphate, potassium phosphate, potassium phosphite, or the like); or fungicides, bactericides, static agents, or bacteriacontrolling agents for suppressing the growth of miscellaneous bacteria such as those belonging to the Family Pseudomonadaceae, Achromobacteraceae, Enterobacteriaceae, Micrococcaceae, Lactobacillaceae, Bacillaceae, or the like. The above-mentioned liquid is appropriately supplied to the culture so as to keep its water content in the range of about 15 – 70% (v/w), preferably 25 – 60% (v/w), throughout the cultivation process.

The amount of the gas introduced into the culture for the purpose of forming a fluidized bed must be regulated appropriately in accordance with the cultivation conditions such as the kind of starting material, the state change of the culture with a laps of time, the water content of culture or the pressure loss of culture. For example, the amount of gas should be increased in the stage where the culture generates a large quantity of heat. In case the starting material is such as, for example, steamed or puffed soy bean, steamed wheat gluten, steamed corn gluten, parched wheat, parched bran, parched barley, or the like having a size of 0.07 to 1.0 mm, the amount of introduced gas is usually in the range of 15 to 70 cm/sec, preferably 20 to 40 cm/sec.

In the invention, said gas may be any of air, oxygen, carbon dioxide, nitrogen and the like or a mixture of two or more of them, and should be selected according to the object of cultivation. Said gas may further be incorporated with a gas for killing miscellaneous bacteria, such as gaseous sulfur dioxide. The culture may have any great layer height, as great as 3 m for example, so far as the culture can form a fluidized bed by the action of the introduced gas. Layer height of the culture should be selected so as to fulfill the economical need.

In the conventional through-flow bed koji-making processes, as is well known, there is used a device for supplying water to the culture layer by which an air, preliminarily conditioned at a humidity of 100% by means of humidity controlling tower, is fed into the culture layer. However, this device is disadvantageous in that an excessive quantity of water is accumulated at the bottom of culture layer which promotes the contamination with miscellaneous bacteria out of the object of the cultivation, and in that the temperature rises particularly in the upper part of the culture as the microorganism grows up so that water in the culture is consumed to cause an excessive dryness of the culture or an unevenness of water content throughout the culture phase, so that the cultivation conditions become difficult to maintain on the optimum level and the enzymatic activity is reduced. On the contrary, if the culture is kept in the state of a fluidized bed and water is supplied while introducing a gas from downside in such a manner as in the case of this invention, the cultivation conditions can be maintained on any arbitrarily chosen level effectively and uniformly, so that the temperature gradient in the vertical direction of the bed can be so small as, for example, about 2° C per 1 m of layer height. Furthermore, water and other additives can be distributed uniformly so that the culture itself can be much saved from contamination. Thus, in the process of this invention the cultivation conditions can be optionally selected as compared with the conventional through-flow bed cultivation process. For example, in the process of this invention a very low water content may be adopted at the beginning stage which can be increased thereafter slowly.

In the course of cultivation, temperature of culture can be maintained in the desired range, usually 25° to 45° C, by controlling the feeds of gas and water (namely, their actual and latent heats) appropriately. Cultivation time may be optionally selected in accordance with the kind of microorganisms used, the object of cultivation, etc. In case where Koji mould is cultivated, the cultivation is usually carried out for about 20 to 80 hours.

The microorganism used in this invention may be any of moulds, yeasts, bacteria, and so on. It should be particularly noted that the process of this invention is applicable with a great readiness even to those of which high layer cultivation is generally considered impossible by the conventional through-flow bed cultivation process, such as the moulds of long stalk-strain belonging to the genera Rhizopus, Mucor and Aspergillus.

The microorganisms particularly suitable for use in the process of this invention include moulds such as *Aspergillus soyae* ATCC 20387 (FERM-P No. 504), *Aspergillus soyae* ATCC 20388 (FERM-P No. 505), *Aspergillus oryzae* ATCC 20386, *Aspergillus oryzae* IAM 2742, *Aspergillus saitoi* R-3813 (ATCC 14332), *Aspergillus niger* NRRL 337, *Aspergillus niger* NRRL 330, *Aspergillus inuii* ATCC 14334, *Aspergillus usamii* ATCC 14331, *Aspergillus awamori* ATCC 14335, *Rhizopus oligosporus* NRRL 2710, *Rhizopus japonicus* IAM 6002, *Rhizopus formosaensis* IAM 6245, *Mucor javanicus* IAM 6108, *Mucor javanicus* HUT 1168; and yeasts such as *Saccharomyces rouxii* IFO 0495, *Saccharomyces rouxii* IFO 0505, *Saccharomyces rouxii* IFO 0506, *Saccharomyces rouxii* IFO 0510, *Saccharomyaces rouxii* IFO 0513, *Saccharomyces rouxii* IFO 0517, *Saccharomyces rouxii* IFO 0570, *Saccharomyces rouxii* OUT 7134, *Saccharomyces rouxii* OUT 7135, *Saccharomyces rouxii* OUT 7136; and bacteria such as *Pediococcus halophilus* ATCC 13624, and *Pediococcus soyae* IAM 1681.

The fluidized bed cultivation apparatus for use in this invention may have any form so far as the content therein can be fluidized. For example, it may have a form of cylinder, rectangular body or the like. Any apparatus of the above-mentioned form may be used so far as it is provided with a gas inlet hole at the bottom, a porous board or a wire netting through which a gas can be introduced into the culture to agitate the latter, and a liquid nozzle inside itself, together with a stirring wheel and an outlet hole for discharging the cultivated product if necessary.

The drawing as attached hereto is a sketch map of an example of the apparatuses.

In the drawing, 1 means a cultivation tank, 2 a porous board or a wire netting, 3 a solid culture in fluidized state, 4 a gas inlet hole, 5 a gas outlet hole, 6 a liquid nozzle, 7 a stirring wheel, 8 an inlet hole of starting materials and 9 an outlet hole of solid culture, respectively.

The process of this invention is advantageous in that there occurs only a very small temperature difference between the upper and the lower parts of the culture so that the layer height of culture can be selected optionally, that water, nutrients, fungicides and the like can be supplied with a great readiness enough to control the growth of microorganism, the production of enzyme, the metabolic products, etc., and that it is applicable to the cultivation of various kinds of microorganisms. Therefore, it is quite useful in industry.

The following examples will illustrate this invention in further detail but do not limit the scope of the invention.

EXAMPLE 1

A koji-making culture material (water content 40.0% v/w) was prepared by pulverizing 75 kg of parched wheat until the particle diameter reached 0.08 to 0.24 mm and then mixing the pulverized wheat with 45 liters of sterilized tap water. The culture material was placed in a cylindrical koji-making vessel having an inner diameter of 34.7 cm and a length of 400.5 cm so that the culture material had a layer height of 196 cm, which was then inoculated with *Aspergillus oryzae* IAM 2742 (conidia number $10^5$/g). Subsequently, a fluidized bed cultivation was carried out continuously for a period of 17 hours, while the culture material was fluidized by introducing air at a temperature of 32° C through a porous board into the vessel from downside at a blowing velocity of 25 cm/sec. Then, aeration was continued at an air temperature of 25° C and at a velocity of 35 cm/sec and, at the same time, an aqueous solution containing 30 ppm aureomycin was continuously sprayed into the fluidized bed by means of a pneumatic atomizing nozzle at a rate of 2.0 liters/hour. Under the above-mentioned conditions, the cultivation was continued for 45 hours in the total. Thus, 83 kg of a koji for use in enzymic preparations (water content of the koji 32.0% v/w) was obtained.

EXAMPLE 2

A koji-making culture material (water content 42.0% v/w) was prepared by pulverizing 70 kg of cooked alpha-rice until its particle diameter reached 0.10 to 0.28 mm and then mixing the pulverized rice with 52 liters of tap water. The culture material was placed in the same koji-making vessel as used in Example 1 (layer height of the culture material: 215 cm) and inoculated with Koji mould (Higuchi Koji, commercial name of a koji manufactured by Higuchi Matsunosuke Shoten; conidia number $10^5$/g). Subsequently, a fluidized bed cultivation was carried out continuously for 20 hours, while air (35° C) was introduced into the vessel from downside at a velocity of 35 cm/sec to fluidize the culture. Then, aeration was continued at an air temperature of 25° C and, at the same time, sterilized tap water was continuously sprayed into the fluidized bed by means of a high-pressure spraying nozzle at a rate of 1.7 liter/hour. Under the above-mentioned conditions the cultivation was continued for 35 hours in the total. Thus, 101 kg of Miso-Koji (water content 32% v/w) was obtained.

EXAMPLE 3

A koji-making culture material (water content 42.0% v/w) was prepared by pulverizing a mixture of 40 kg of puffed, denatured and defatted soy bean and 30 kg of parched wheat until the particle diameter reached 0.10 to 0.28 mm, and then adding 45.5 liters of tap water to the pulverized mixture. The culture material was placed in the same koji-making vessel as used in Example 1 (layer height of the culture material: 203 cm) and inoculated with *Aspergillus soyae* ATCC 20387 (FERM-P No. 504), (a seed koji for use in the production of soy sauce; conidia number $10^5$/g). Subsequently, a fluidized bed cultivation was carried out continuously for 20 hours, while air (35° C) was introduced from the bottom of the koji-making vessel at a velocity of 30 cm/sec to fluidize the culture material. Then, aeration was continued at an air temperature of 25° C and, at the same time, sterilized tap water was continuously sprayed into the fluidized bed by means of a high-pressure spraying nozzle at a rate of 0.6 liter/hour. Under the above-mentioned conditions, the cultivation was continued for 45 hours in the total. Thus, 81 kg of soy sauce koji (water content of the koji 28% v/w) was obtained.

EXAMPLE 4

A koji-making culture material (water content 42.0% v/w) was prepared by pulverizing a mixture of 40 kg of puffed, denatured and defatted soy bean and 30 kg of parched wheat until the particle diameter reached 0.10 to 0.28 mm and then adding 45.5 liters of tap water to the pulverized mixture. The culture material was placed in the same koji-making vessel as used in Example 1 (layer height of the culture material: 207 cm) and was inoculated with *Aspergillus soyae* ATCC 20387 (FERM-P No. 504, conidia number $10^6$/g), which is a seed culture for use in the production of soy sauce, *Pediococcus soyae* IAM 1681 (cell number 10/g) which is lactobacillus for use in the production of soy sauce, and *Saccharomyces rouxii* ATCC 13356 (cell number $10^3$/g) which is a yeast for use in the production of soy sauce. Subsequently, air (37° C) was introduced into the koji-making bed at a velocity of 35 cm/sec for 15 hours to fluidize the culture, after which air (35° C) was continuously introduced for 5 hours. Subsequently, air (24° C) was continuously introduced and, at the same time, an aqueous solution of ammonia of 0.1% (v/v) was continuously sprayed at a rate of 0.8 liter/hour. Under the above-mentioned conditions the cultivation was continued for 48 hours in the total. Thus, 80 kg of a soy sauce koji (water content 29% v/w) was obtained.

EXAMPLE 5

A culture material (water content 35.0% v/w) was prepared by pulverizing a mixture of 40 kg of parched wheat and 50 kg of wheat bran, which had been cooked and sterilized in advance in an autoclave, until the particle diameter reached 0.17 to 0.40 mm and then adding 45 liters of tap water to the pulverized mixture. The culture material was placed in the same koji-making vessel as used in Example 1 (layer height of the culture material: 191 cm) and was inoculated with *Aspergillus saitoi* R-3813 (ATCC 14332, conidia number $10^5$/g). Subsequently, air (35° C) was introduced from the bottom of the koji-making vessel continuously at a velocity of 30 cm/sec until 20 hours had elapsed after the start of cultivation. Then, aeration was continued at an air temperature of 24° C and, at the same time, 1/100 M McIlvain buffer solution (pH 5.5), which had been sterilized in advance in an autoclave, was continuously sprayed at a rate of 1.9 liter/hour. Under the above-mentioned conditions the cultivation was continued for 50 hours in the total. Thus, 98 kg of a cultivated product for use in enzymic preparations (water content 28% v/w) was obtained.

EXAMPLE 6

A koji-making culture material (water content 42.0% v/w) was prepared by pulverizing a mixture of 40 kg of puffed, denatured and defatted soy bean and 30 kg of parched wheat until the particle diameter reached 0.10 to 0.28 mm, and then adding 45.5 liters of tap water to the pulverized mixture. The culture material was placed in the same koji-making vessel as used in Example 1 (layer height of the culture material: 203 cm) and inoculated with *Aspergillus soyae* ATCC 20388 (FERM-P No. 505), (a seed koji for use in the production of soy sauce; conidia number $10^5$/g). Subsequently, a fluidized bed cultivation was carried out continuously for 15 hours, while air (35° C) was introduced from the bottom of the koji-making vessel at a velocity of 30 cm/sec to fluidize the culture material. Then, aeration was continued at an air temperature of 25° C and, at the same time, sterilized tap water was continuously sprayed into the fluidized bed by means of a high-pressure spraying nozzle at a rate of 1.2 liter/hour for further 10 hours, at a rate of 1.5 liter/hour for further 10 hours, and at a rate of 1.0 liters/hour for further 10 hours (45 hours in the total). Thus, 138 kg of soy sauce koji (water content of the koji 58.0% v/w) was obtained.

What is claimed is:

1. A process for producing a koji for use in enzymic preparations by means of fluidized bed comprising cultivating a microorganism on a solid culture medium while mixing the solid culture medium in a fluidized bed with an upward gas stream and supplying an atomized liquid into the solid culture.

2. A process according to claim 1, wherein said atomized liquid is an aqueous liquid and the quantity of the liquid supplied to the solid culture is in the range of 10 to 250% (v/w).

3. A process according to claim 1, wherein the quantity of the liquid supplied to the solid culture is in the range of 15 to 150% (v/w).

4. A process according to claim 1, wherein the starting material of the solid culture is at least one member selected from the group consisting of globular soy bean, defatted soy bean, wheat gluten, corn gluten, concentrated proteins, isolated proteins, wheat, bran, barley, rice and starch.

5. A process according to claim 1, wherein at least one member selected from the group consisting of inorganic salts and vitamins is added to the solid culture.

6. A process according to claim 1, wherein the starting material of said culture medium has an average particle diameter of 0.07 to 1.0 mm.

7. A process according to claim 1, wherein the starting material of said culture has an average particle diameter of 0.1 to 0.5 mm.

8. A process according to claim 1, wherein the gas is at least one member selected from the group consisting of air, oxygen, carbon dioxide and nitrogen.

9. A process according to claim 1, wherein the gas is incorporated with sulfur dioxide.

10. A process according to claim 1, wherein the amount of gas introduced is in the range of 15 to 70 cm/sec.

11. A process according to claim 1, wherein the liquid is either water itself or water incorporated with at least one member selected from the group consisting of minerals, vitamins, amino acids, the culture itself, organic salts, inorganic salts, fungicides, bactericides, static agents and bacteria-controlling agents.

12. A process according to claim 1, wherein the liquid is supplied to the solid culture so as to maintain the water content of the solid culture in the range of 15 to 70% (v/w).

13. A process according to claim 1, wherein the cultivation is carried out at a temperature of 25° C to 45° C.

14. A process according to claim 1, wherein the cultivation is carried out for 20 to 80 hours.

15. A process according to claim 1, wherein the microorganism is a mould, a yeast or a bacterium.

16. A process according to claim 1, wherein the microorganism is a mould.

17. A process according to claim 16, wherein the mould is of long stalk-strain belonging to the genus Rhizopus, Mucor or Aspergillus.

18. A process according to claim 1, wherein the microorganism is *Aspergillus soyae* ATCC 20387 (FERM-P No. 504), *Aspergillus soyae* ATCC 20388 (FERM-P No. 505), *Aspergillus oryzae* ATCC 20386, *Aspergillus oryzae* IAM 2742, *Aspergillus saitoi* R-3813 (ATCC 14332), *Aspergillus niger* NRRL 337, *Aspergillus niger* NRRL 330, *Aspergillus inuii* ATCC 14334, *Aspergillus usamii* ATCC 14331, *Aspergillus awamori* ATCC 14335, *Rhizopus oligosporous* NRRL 2710, *Rhizopus japonicus* IAM 6002, *Rhizopus formosaensis* IAM 6245, *Mucor javanicus* IAM 6108, *Mucor javanicus* HUT 1168, *Saccharomyces rouxii* IFO 0495, *Saccharomyces rouxii* IFO 0505, *Saccharomyces rouxii* IFO 0506, *Saccharomyces rouxii* IFO 0510, *Saccharomyces rouxii* IFO 0513, *Saccharomyces rouxii* IFO 0517, *Saccharomyces rouxii* IFO 0570, *Saccharomyces rouxii* OUT 7134, *Saccharomyces rouxii* OUT 7135, *Saccharomyces rouxii* OUT 7136, *Pediococcus halophilus* ATCC 13624, or *Pediococcus soyae* IAM 1681.

19. A process for producing a soy sauce koji by means of fluidized bed comprising cultivating a microorganism on a solid culture medium while mixing the solid culture medium in a fluidized bed with an upward gas stream and supplying an atomized liquid into the solid culture.

20. A process according to claim 19, wherein said atomized liquid is an aqueous liquid and the quantity of the liquid supplied to the solid culture is in the range of 10 to 250% (v/w).

21. A process according to claim 19, wherein the quantity of the liquid supplied to the solid culture is in the range of 15 to 150% (v/w).

22. A process according to claim 19, wherein the starting material of the solid culture is at least one member selected from the group consisting of globular soy bean, defatted soy bean, wheat gluten, corn gluten, concentrated proteins, isolated proteins, wheat, bran, barley, rice and starch.

23. A process according to claim 19, wherein at least one member selected from the group consisting of inorganic salts and vitamins is added to the solid culture.

24. A process according to claim 19, wherein the starting material of said culture medium has an average particle diameter of 0.07 to 1.0 mm.

25. A process according to claim 19, wherein the starting material of said culture medium has an average particle diameter of 0.1 to 0.5 mm.

26. A process according to claim 19, wherein the gas is at least one member selected from the group consisting of air, oxygen, carbon dioxide and nitrogen.

27. A process according to claim 19, wherein the gas is incorporated with sulfur dioxide.

28. A process according to claim 19, wherein the amount of gas introduced is in the range of 15 to 70 cm/sec.

29. A process according to claim 19, wherein the liquid is either water itself or water incorporated with at least one member selected from the group consisting of minerals, vitamins, amino acids, the culture itself, organic salts, inorganic salts, fungicides bactericides, static agents and bacteria-controlling agents.

30. A process according to claim 19, wherein the liquid is supplied to the solid culture so as to maintain the water content of the solid culture in the range of 15 to 70% (v/w).

31. A process according to claim 19, wherein the cultivation is carried out at a temperature of 25° C to 45° C.

32. A process according to claim 19, wherein the cultivation is carried out for 20 to 80 hours.

33. A process according to claim 19, wherein the microorganism is a mould, a yeast or a bacteriaum.

34. A process according to claim 19, wherein the microorganism is a mould.

35. A process according to claim 33, wherein the mould is of long stalk-strain belonging to the genus *Aspergillus*.

36. A process according to claim 19, wherein the microorganism is *Aspergillus soyae* ATCC 20387 (FERM-P No. 504), *Aspergillus soyae* ATCC 20388 (FERM-P No. 505), *Aspergillus oryzae* ATCC 20386, *Aspergillus oryzae* IAM 2742, *Aspergillus saitoi* R-3813 (ATCC 14332), *Aspergillus niger* NRRL 337, *Aspergillus niger* NRRL 330, *Aspergillus inuii* ATCC 14334, *Aspergillus usamii* ATCC 14331, *Aspergillus awamori* ATCC 14335, *Saccharomyces rouxii* IFO 0495, *Saccharomyces rouxii* IFO 0505, *Saccharomyces rouxii* IFO 0506, *Saccharomyces rouxii* IFO 0510, *Saccharomyces rouxii* IFO 0513, *Saccharomyces rouxii* IFO 0517, *Saccharomyces rouxii* IFO 0570, *Saccharomyces rouxii* OUT 7134, *Saccharomyces rouxii* OUT 7135, *Saccharomyces rouxii* OUT 7136, *Pediococcus halophilus* ATCC 13624, or *Pediococcus soyae* IAM 1681.

37. A process for producing a Miso-koji by means of fluidized bed comprising cultivating a microorganism on a solid culture medium while mixing the solid culture medium in a fluidized bed with an upward gas stream and supplying an atomized liquid into the solid culture.

38. A process according to claim 37, wherein the microorganism is *Aspergillus soyae* ATCC 20387 (FERM-P No. 504), *Aspergillus soyae* ATCC 20388 (FERM-P No. 505), *Aspergillus oryzae* ATCC 20386, *Aspergillus oryzae* IAM 2742, *Aspergillus saitoi* R-3813 (ATCC 14332), *Aspergillus niger* NRRL 337, *Aspergillus* niger NRRL 330, *Aspergillus inuii* ATCC 14334, *Aspergillus usamii* ATCC 14331, *Aspergillus awamori* ATCC 14335, *Saccharomyces rouxii* IFO 0495, *Saccharomyces rouxii* IFO 0505, *Saccharomyces rouxii* IFO 0506, *Saccharomyces rouxii* IFO 0510, *Saccharomyces rouxii* IFO 0513, *Saccharomyces rouxii* IFO 0517, *Saccharomyces rouxii* IFO 0570, *Saccharomyces rouxii* OUT 7134, *Saccharomyces rouxii* OUT 7135, *Saccharomyces rouxii* OUT 7136, *Pediococcus halophilus* ATCC 13624, or *Pedicoccus soyae* IAM 1681.

39. A process according to claim 38 wherein said atomized liquid is an aqueous liquid and the quantity of liquid supplied to the culture is in the range of 10 to 250% (v/w).